(12) United States Patent
Foos et al.

(10) Patent No.: US 8,845,190 B2
(45) Date of Patent: Sep. 30, 2014

(54) LOW-DOSE AUTOMATIC EXPOSURE CONTROL SYSTEM FOR DIGITAL PORTABLE X-RAY IMAGING

(75) Inventors: David H. Foos, Webster, NY (US); Xiaohui Wang, Pittsford, NY (US); William J. Sehnert, Fairport, NY (US)

(73) Assignee: Carestream Health, Inc., Rochester, NY (US)

( * ) Notice: Subject to any disclaimer, the term of this patent is extended or adjusted under 35 U.S.C. 154(b) by 299 days.

(21) Appl. No.: 13/252,368

(22) Filed: Oct. 4, 2011

(65) Prior Publication Data

US 2012/0087474 A1 Apr. 12, 2012

Related U.S. Application Data

(60) Provisional application No. 61/390,219, filed on Oct. 6, 2010.

(51) Int. Cl.
*H05G 1/60* (2006.01)
*G01D 18/00* (2006.01)
*G06K 9/60* (2006.01)
*G06K 9/40* (2006.01)
*A61B 6/00* (2006.01)

(52) U.S. Cl.
CPC ............. *A61B 6/4405* (2013.01); *A61B 6/542* (2013.01); *A61B 6/545* (2013.01); *A61B 6/488* (2013.01)
USPC .......................... 378/207; 378/98.12; 382/131

(58) Field of Classification Search
USPC ......... 378/51, 56, 62, 91, 95–98, 98.8, 98.12, 378/106, 204, 207, 210; 250/370.01, 250/370.06, 370.07, 370.08, 370.09, 371; 382/128, 132, 270–275, 307, 325
See application file for complete search history.

(56) References Cited

U.S. PATENT DOCUMENTS

| 4,649,558 | A | * | 3/1987 | Brunn et al. | 378/97 |
| 6,069,933 | A | | 5/2000 | Schultz | |
| 6,459,765 | B1 | | 10/2002 | Ganin et al. | |
| 6,501,819 | B2 | | 12/2002 | Unger et al. | |
| 6,501,829 | B2 | * | 12/2002 | Matsumoto et al. | 378/154 |
| 6,580,779 | B2 | | 6/2003 | Avinash et al. | |
| 7,133,490 | B2 | | 11/2006 | Muller et al. | |
| 7,431,500 | B2 | | 10/2008 | Deych et al. | |
| 7,519,155 | B2 | | 4/2009 | Mollus et al. | |
| 2002/0075997 | A1 | | 6/2002 | Unger et al. | |
| 2009/0136112 | A1 | * | 5/2009 | Bismuth et al. | 382/132 |

OTHER PUBLICATIONS

Martin Uffmann, et al., "Digital radiography: The balance between image quality and required radiation Dose," European Journal of Radiology, 2009, vol. 72, pp. 202-208.
International Search Report completed on Apr. 30, 2012 for International Application No. PCT/US2011/054895, 2 pages.

* cited by examiner

*Primary Examiner* — Anastasia Midkiff

(57) ABSTRACT

A method for obtaining a radiographic image, the method executed at least in part on a computer, generates a first exposure and acquires image data from the first exposure as a first component image. A second exposure is generated using one or more parameters that are adjusted according to an image quality characteristic of the acquired image data from the first exposure. Image data is acquired from the second exposure as a second component image. One or more additional exposures are generated and an additional component image acquired with each additional exposure. A composite image is formed by combining image data content from the first and second component images and the one or more additional component images.

18 Claims, 8 Drawing Sheets

FIG. 2A *(Prior Art)*

LOW-DOSE AUTOMATIC EXPOSURE CONTROL SYSTEM FOR DIGITAL PORTABLE X-RAY IMAGING

CROSS REFERENCE TO RELATED APPLICATIONS

This application claims the benefit of U.S. Provisional Patent Application Ser. No. 61/390,219, filed on Oct. 6, 2010, entitled LOW DOSE AUTOMATIC EXPOSURE CONTROL SYSTEM FOR DIGITAL PORTABLE X-RAY IMAGING in the names of Foos, Wang, and Sehnert, the contents of which are incorporated fully herein by reference.

FIELD OF THE INVENTION

The invention relates generally to the field of radiographic imaging and more particularly relates to apparatus and methods for achieving reduced exposure using pulsed radiation.

BACKGROUND OF THE INVENTION

Automatic Exposure Control (AEC) apparatus are widely used in conventional diagnostic X-ray equipment to control X-ray exposure levels received by a patient. Using an AEC device can help to limit the amount of radiation that is received by sensing the radiation level at a suitable location in the exposure path and providing an output signal that indicates when sufficient radiation has been received. This output signal is then used to disable power to the X-ray emission components, thereby stopping the generation of ionizing radiation.

There are often practical and physical difficulties in positioning an automatic exposure control (AEC) device when imaging patients in an intensive care unit (ICU). Therefore, such AEC devices, while commercially available, are rarely used in many ICU environments. Instead, the technologist generally uses an estimate based on experience with different types of imaging and on the patient's overall build. Instead of using the feedback available from AEC devices, the radiographic technologist manually sets exposure technique parameters (kVp and mAs) on the portable x-ray machine.

It is known that there is a significant degree of variability in the manual selection of exposure techniques, as it is the technologist who visually assesses the thickness of the patient before making the selections. The combination of the patient thickness, the type of imaging receptor (e.g., computed radiography (CR), or digital radiography (DR)), and the choice of exposure techniques directly influences both the noise appearance and contrast in the captured image.

Once the image is captured, the technologist makes a visual assessment of the image quality, and may also refer to an exposure indicator (EI) to determine if the image was properly exposed. The exposure indicator is a figure of merit that is calculated for the captured image and that is related to the average signal level for the anatomical region of interest.

The technologist may decide to repeat the image if the EI is too low, or if the image appears noisy, i.e., if the image is deemed to be underexposed.

To reduce the number of images that may need to be repeated because of underexposure, and because there is some variability associated with the choice of exposure parameters, it is a typical practice to set the exposure parameters well-above the minimum level that is required to produce a diagnostic quality image. Consequently, patients that are imaged using portable x-ray machines may often receive a considerably higher radiation dose than that which is required for diagnosis. This can be a particular problem in intensive care units, where patients typically receive one or more chest x-rays per day, including pediatric and neonatal intensive care unit patients.

In mammography and other specialized radiography applications, one or more initial sampling exposures are sometimes obtained and assessed in order to help determine what technique settings are most appropriate for a particular patient. This can include settings such as kVp and mAs technique settings, for example. In such applications, at least one low-dosage initial exposure, sometimes termed a "scout view", is first obtained, then examined by an operator or processed as a guideline to minimizing exposure or to targeting exposure for characteristic organ characteristics such as density or for particular regions of interest (ROI) of the patient's anatomy. This initial image is typically discarded once analysis is completed and the actual radiographic image of the patient is then obtained. While this method has some value, there are drawbacks. Operator assessment of the subject from a low-dosage image requires good judgment, complicates the image acquisition and processing workflow, and adds to the overall cost of radiographic imaging. The initial low-dose exposure adds to the overall amount of exposure required.

There is, then, a need for apparatus and methods that help to reduce the overall amount of exposure needed in the portable x-ray environment, without compromising the quality of images obtained.

SUMMARY OF THE INVENTION

Certain embodiments described herein address the need for exposure control without requiring separate apparatus for exposure measurement and feedback. Embodiments of the present invention utilize image data obtained by the digital detector to determine when it is appropriate to terminate radiation.

Advantageously, certain embodiments described herein can eliminate the need for a separate AEC device for exposure measurement. Accumulated image data from the digital imaging detector itself is used to determine when exposure is sufficient based on one or more image quality characteristics.

Such non-limiting aspects are given only by way of illustrative example, and such objects may be exemplary of one or more embodiments of the invention. Other desirable objectives and advantages inherently achieved by the disclosed embodiments may occur or become apparent to those skilled in the art. The invention is defined by the appended claims.

According to one aspect of exemplary embodiments, there is provided a method for obtaining a radiographic image of a patient's anatomy, the method executed at least in part on a computer and comprising:

generating a series of N successive exposures [1 ... N] and acquiring each of N corresponding images as a component image, wherein for the second exposure n=2 and for each subsequent exposure n in [1 ... N], one or more exposure setup parameters is conditioned based on an evaluation of one or more image quality characteristics from at least one previous exposure n−1.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 2A has timing diagrams that show continuous and accumulated exposure for conventional radiographic imaging.

DESCRIPTION OF EXEMPLARY EMBODIMENTS

Figure 1:
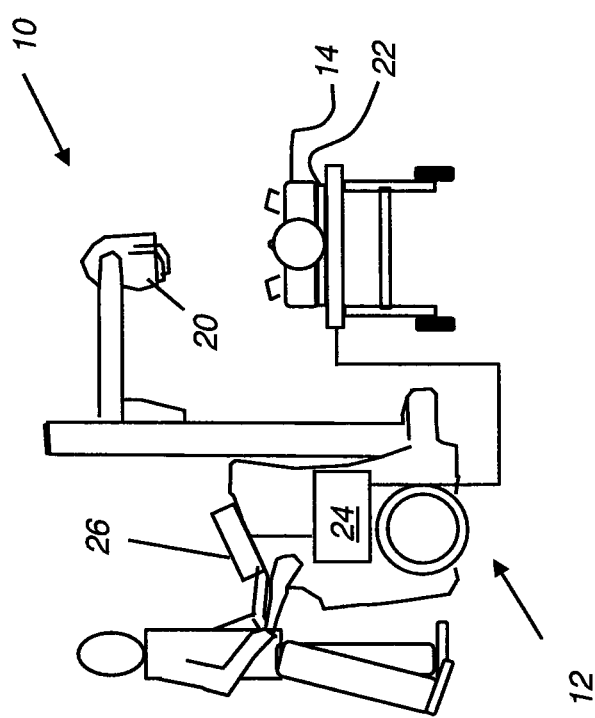
FIG. 1 is a schematic diagram that shows a portable digital radiography system that uses an embodiment of the present invention.

The following is a detailed description of exemplary embodiments, reference being made to the drawings in which the same reference numerals identify the same elements of structure in each of the several figures.

Exemplary embodiments can take advantage of the speed and image processing and refresh capabilities of the digital radiography (DR) detector to provide a method that allows dynamic adjustment of exposure settings and to help reduce the amount of radiation used for radiographic imaging. To do this, exemplary embodiments described herein can calculate a figure of merit (FOM) that is indicative of image quality and of the overall exposure received.

As noted in the background section, the conventional workflow requires some decision-making for exposure settings on the part of the technician and, because there is no feedback signal from an AEC device, provides no indication of suitable exposure levels until image capture has already been completed. Therefore, conventional methods can tend to either over- or under-expose the patient and often require re-takes. Even methods that use an initial low-dosage exposure for assessment of proper settings can add to the exposure required.

Certain embodiments described herein can address this problem by forming the radiographic image as a composite image, accumulating image data from two or more successive, rapidly generated pulses of radiation. Following at least the first exposure pulse, at least a representative portion of the accumulated image data set can be evaluated or checked and an image quality characteristic is analyzed from the image data and used to determine whether or not a desired level of image quality can be achieved, how many additional pulses are needed, and how these pulses need to be conditioned. A number of these steps are optional, depending on how closely the radiographic imaging apparatus monitors results from each individual pulse and cumulative results from multiple pulses, with the image data set from each exposure pulse combined with image data sets from previous exposure pulses.

The schematic diagram of FIG. 1 shows a portable digital radiography (DR) apparatus 10. A cart 12 allows portability of a pulsed x-ray source 20 for imaging anatomy of a patient 14, such as in an ICU facility, for example. A DR detector 22 provides image data in response to the exposure radiation. A control logic processor 24 controls the response of portable digital radiography (DR) apparatus 10 according to operator instructions and according to feedback data received from DR detector 22. A display 26 is in signal communication with control logic processor 24 and can be energized for display of a composite image that can be formed from the separate component images accumulated for each exposure pulse.

In one embodiment, x-ray source 20 is energizable to provide a series of exposure pulses, wherein each pulse has a duration within 0.1 seconds. Digital detector 22 is energizable to provide an image data set corresponding to each exposure pulse. Control logic processor 24 is energizable to acquire each image data set as a component image between exposure pulses and to combine the series of component images to form a composite image.

In the conventional exposure sequence, shown in an exposure timing graph 30 in FIG. 2A, exposure begins at a time t0 and is continuous, at the same power level L, until it terminates at a time T. Time T may be a preset time or may depend on a feedback signal from an automatic exposure control device when the accumulated exposure E, shown in an exposure graph 34, is sufficient. As noted in the background section, automatic exposure control (AEC) devices are not often used with portable DR systems; thus, time T is typically a time-out interval assigned as part of the setup process and the exposure E value is set at least somewhat above what is needed in most cases.

Figure 2B:
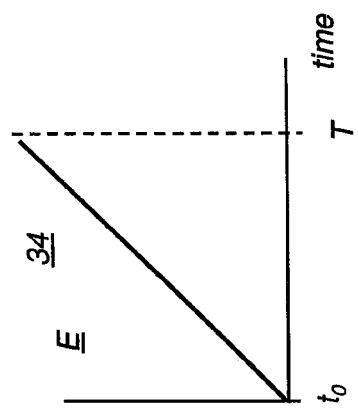
FIG. 2B has timing diagrams that show pulsed and corresponding accumulated exposure according to an embodiment of the present invention.
Figure 2B:
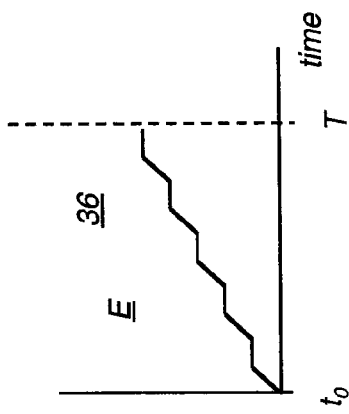
Figure 2B:
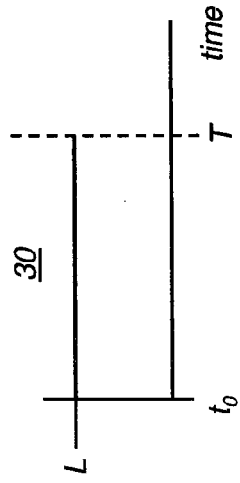
Figure 2B:
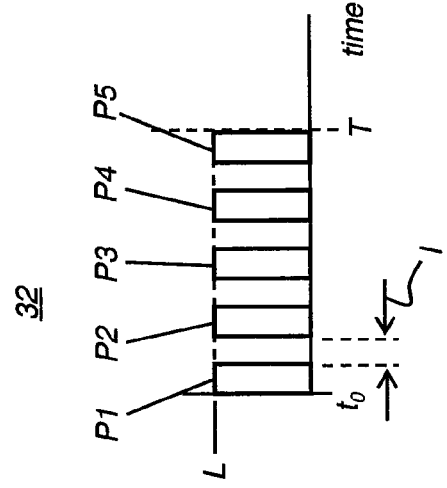

By comparison, FIG. 2B shows the timing of an exposure sequence, in an exposure timing graph 32, for obtaining an image as a composite image from a set of multiple component images, according to an embodiment of the present invention. To do this, x-ray source 20, instead of being on continuously as shown in FIG. 2A, is pulsed a number of times, providing low-intensity radiation, until the needed exposure energy E is accumulated, as shown in an exposure graph 36. By way of example, FIG. 2B shows five pulses, P1, P2, P3, P4, and P5; in practice, two or more pulses can be used for obtaining the accumulated image data. With each exposure pulse, a component image is formed and added to the accumulated image data. Pulses are of a short duration, such as nominally 0.03 seconds or less. Pulse durations are less than 0.1 second in one embodiment.

As shown in graph 36 of FIG. 2B, exposure E accumulates with each radiation pulse. In an interval I between any two pulses $P_{n-1}$ and $P_n$, at least some portion of the image data for a component image can be evaluated (e.g., read) from DR detector 22 (FIG. 1) and contrast, or some other suitable image characteristic, is used to determine whether or not a subsequent pulse is needed.

Contrast-to-noise ratio (CNR) is one image characteristic of particular value as a figure of merit for this purpose. The component images obtained from each respective pulse are combined together to provide intermediate, accumulated image data for contrast assessment and to form the composite image when exposure is complete. When the CNR value for the accumulated image data exceeds a desired threshold level, exposure is completed. The composite image can then be formed by combining its corresponding component images.

In order to meet the response time requirements for pulsed imaging and dynamic assessment of exposure settings, pulses are preferably executed over a very short time interval so that patient movement does not interfere with image quality. In one embodiment, for example, five pulses are provided, with intervals for reading data between, within one second. DR detector 22 must be able to provide the needed image characteristic information following each pulse P. Control logic processor 24 (FIG. 1) or an additional logic processor (e.g., on the detector 22) can then be able to process the received image data and indicate whether or not an additional pulse of radiation is needed. Other aspects of component image processing are described subsequently.

Figure 3:
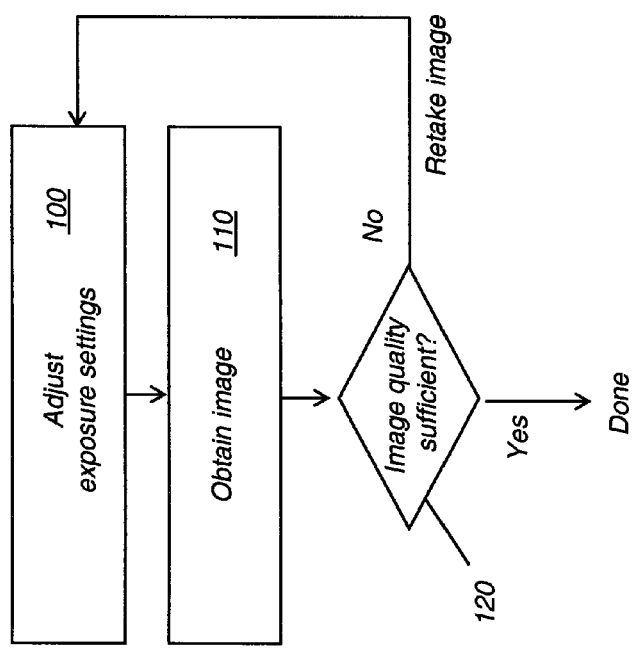
FIG. 3 is a logic flow diagram that shows the execution sequence for conventional imaging using a portable DR system.

FIG. 3 is a logic flow diagram showing steps for conventional capture of a portable x-ray image. In an initial setup step 100, the technician assesses the overall build of the patient, then uses factors such as the relative thickness of the patient as a guide to making the necessary exposure settings, such as kVp and mAs settings and a timing value, for example. Once these settings have been made, the technician obtains the image in an image capture step 110. A quality evaluation step 120 follows, in which the obtained image undergoes a visual assessment of noise and other image quality characteristics, and an exposure index (EI) is calculated. If the image is acceptable, conventional image capture is complete. If the image is unacceptable, the image is re-taken with settings adjusted in setup step 100. Quality evaluation step 120 may use all of the image data for the component image or may sub-sample the component image in order to make its quality determination.

Figure 4A:
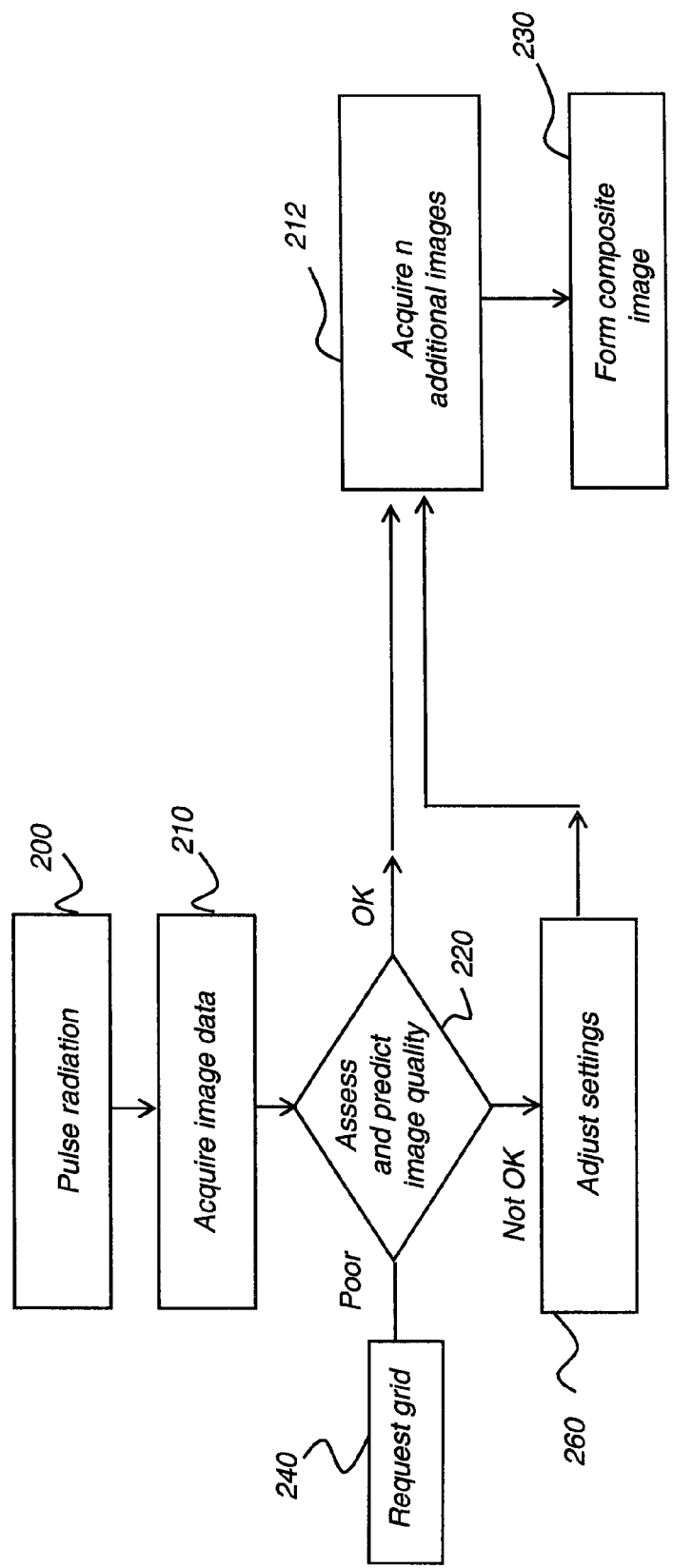
FIG. 4A is a logic flow diagram that shows the execution sequence for imaging using pulsed radiation according to an embodiment of the present invention.

FIG. 4A is a logic flow diagram showing steps for forming the composite image from two or more component images with exposure monitoring using another exemplary embodiment. A single pulse of radiation is provided in a pulse radiation step 200 and image data from the initial pulse is obtained in an image acquisition step 210. An assessment step 220 follows, in which the obtained initial image is assessed for image quality. Consistent with one embodiment, image contrast is measured in assessment step 220 and the measurement is used to predict the exposure energy needed to provide an acceptable image. From this predictive measurement, one of three outcomes is possible:

(i) Image quality is poor and it is unlikely that contrast will achieve a predetermined threshold with a number of additional images from pulsed radiation, regardless of changes to technique settings. This can be the case, for example, when the image data obtained from the initial pulse shows that some number of successive pulses will not achieve an image having suitable contrast. In this case, the system executes a grid request step 240, providing a signal indicating to the technician that a grid is highly recommended for this particular image. A message can display, for example, on display 26 (FIG. 1) indicating the need for a grid. The obtained image is considered to be from a pre-image exposure and is discarded, since it cannot be used as a component image for forming the composite image.

(ii) Image quality is poor, but changes to technique settings can provide an acceptable output composite image. In this case, settings are adjusted in an adjustment step 260. For example, the mAs or kVp values can be changed according to a predictive contrast-to-noise measurement.

(iii) Image quality is acceptable and some number n of additional component images can be acquired. This number n for subsequent pulses is computed in assessment step 220, based on results from the initial pulse in pulse step 200 and image acquired in image acquisition step 210.

Following outcome (ii) or (iii) above, image acquisition step 212 executes, obtaining the n additional images needed for providing the final composite image. As part of image acquisition step 212, an assessment can be made following each acquired image to determine whether or not additional exposure pulses are required or exposure terminated. According to one embodiment of the present invention, for example, a cumulative assessment of CNR is made as a predictive measurement following each component image acquisition. Optionally, the initial assessment of the initial component image in step 220 may dictate a specific number of additional pulsed exposures, without further assessment of subsequent component images or of the accumulated image data in the pulsed exposure and image acquisition sequence. Once the needed images are acquired, a form composite image step 230 executes, forming the composite image that can then be displayed or processed. This can end processing for the particular radiographic image.

In an alternate embodiment, adjustment step 260 is not automatically performed by portable DR apparatus 10, but must be performed by the technician. Thus, for example, steps 200, 210, and 220 in FIG. 4A may be executed to provide information to the operator to adjust a kVp setting to a more appropriate value. Repeating the sequence may then allow the process to move automatically from assessment step 220 to image acquisition step 212.

Figure 4B:
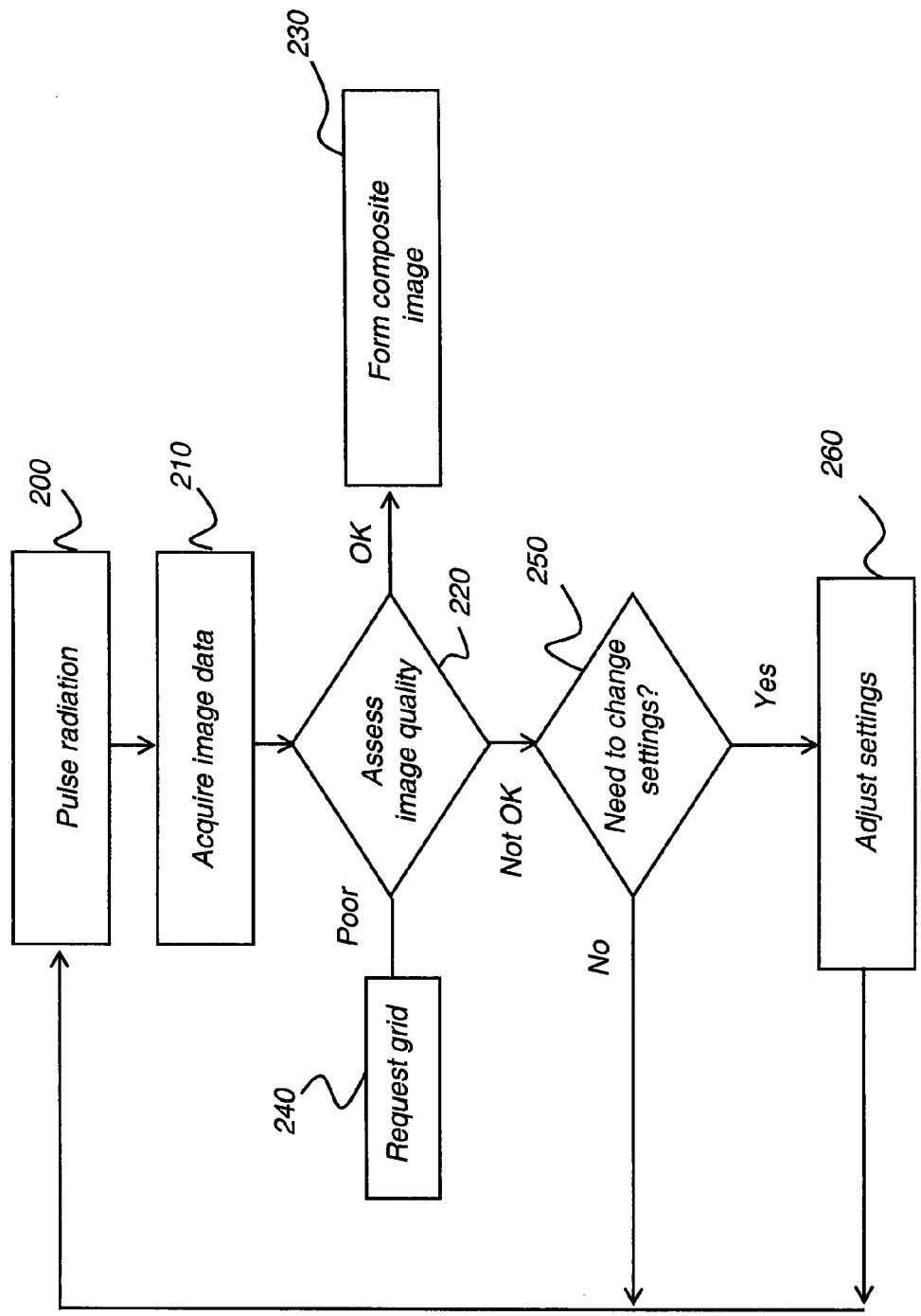
FIG. 4B is a logic flow diagram that shows the execution sequence for imaging using pulsed radiation according to an alternate embodiment of the present invention in which each pulse is assessed.

FIG. 4B is a logic flow diagram showing steps for forming the composite image from two or more component images with exposure monitoring using an alternate exemplary embodiment. In the FIG. 4B embodiment, each successive image is assessed, along with cumulative information from previous images, to determine the settings for each image and the termination point for the image acquisition process.

Referring to FIG. 4B, a single pulse of radiation is provided in pulse radiation step 200 and image data from the pulse is obtained in image acquisition step 210. The obtained image data is also combined with image data from one or more previous pulse radiation steps 200, if any. Assessment step 220 follows, in which the obtained image, from one or more pulses, is assessed for image quality. Where the CNR or other image quality measure is satisfactory, exposure is ended and form composite image step 230 executes, forming the composite image that can then be displayed or processed. This ends processing for the particular image. Where image quality is very poor, and only the first pulse has been obtained, the system executes an optional grid request step 240, indicating to the technician that a grid is highly recommended for this particular image, as noted previously. This can be the case, for example, when the first pulse clearly shows that some number of successive pulses will not achieve an image having suitable contrast. Where the CNR is achievable but image quality may be less than what is needed, execution passes to an optional settings decision step 250. If there is no need to change exposure settings, such as mAs, kVp, or other value, the next pulse radiation step 200 executes. Otherwise, one or more settings values may be adjusted in an optional adjustment step 260 before the process repeats. Using this sequence, a series of N successive exposures [1 . . . N] generates each of N corresponding images as a component image. For the second exposure n=2 and for each subsequent exposure n in [1 . . . N], one or more exposure setup parameters can be conditioned based on an assessment or evaluation of one or more image quality characteristics from at least one previous exposure n−1.

It must be emphasized that the system arrangement that is shown in FIG. 1 is exemplary and represents a number of possible arrangements for elements of a portable radiography system that can use the dose control approach described herein. For example, control logic processor 24, shown as part of cart 12 in FIG. 1, can be embodied in any number of ways, including dedicated processors or microprocessors, networked processors, and computers and workstations of various types, for example. According to one embodiment herein, the processing logic for exposure control is provided on-board DR detector 22, reducing or eliminating the need for fast data transfer from detector 22 during the brief interval between pulses.

As was described with reference to the logic flow of the embodiment of FIG. 4B, the described settings adjustment can be implemented one or more times in the chain of pulses that form a composite image. Referring back to FIG. 2B, for example, each pulse P1-P5 can be at a different exposure energy level. Moreover, each pulse width can be different. Thus, for example, it can be advantageous to provide an initial pulse of a given exposure power and time interval, then to provide second, third, and additional pulses based on the analysis of image data from the initial pulse. The initial pulse can provide a small fraction of the needed exposure; alternately, the initial pulse can provide a substantial amount of the needed exposure energy (e.g., 5%, 10%, 20%, 50%, 70%, etc.), so that component image data from subsequent pulses improve the CNR or other characteristic. With reference to the sequence of FIG. 4B, this would make steps 250 and 260 optional for second and later pulses, for example. Then, assessment step 220 simply checks to determine whether or not image quality is sufficient based on the accumulated image data. Exemplary method and/or apparatus embodiments herein can address difficulties in positioning that were previously described, and thus, exemplary embodiments can reduce the likelihood of overexposure or underexposure.

The response speed of image acquisition electronics may determine whether or not down-sampling of the image data is useful for determining the number of pulses and corresponding technique settings. It may be practical, for example, to use a subset of the accumulated image data for assessment during processing, rather than requiring that all of the accumulated image data be used for this purpose. For example, form composite image step 230 may take a longer time to execute than is needed for CNR assessment between pulses.

Various options can be employed in the choice of a characteristic image quality indicator, such as CNR. However, the image quality indicator is preferably computed rapidly and is largely invariant to the uncertainties in the patient and detector positioning. Resolution can be reduced in order to help speed calculation, for example. A region of interest (ROI) can be identified in the obtained image, so that contrast or other characteristic is assessed only over a portion or two or more portions of the image. Different image quality characteristics can be measured on the same image or the same image quality characteristic can be measured in multiple places on the image, including with different thresholds for acceptability. For example, in a chest x-ray, local CNR values may vary over different portions of the anatomy.

Figure 5:
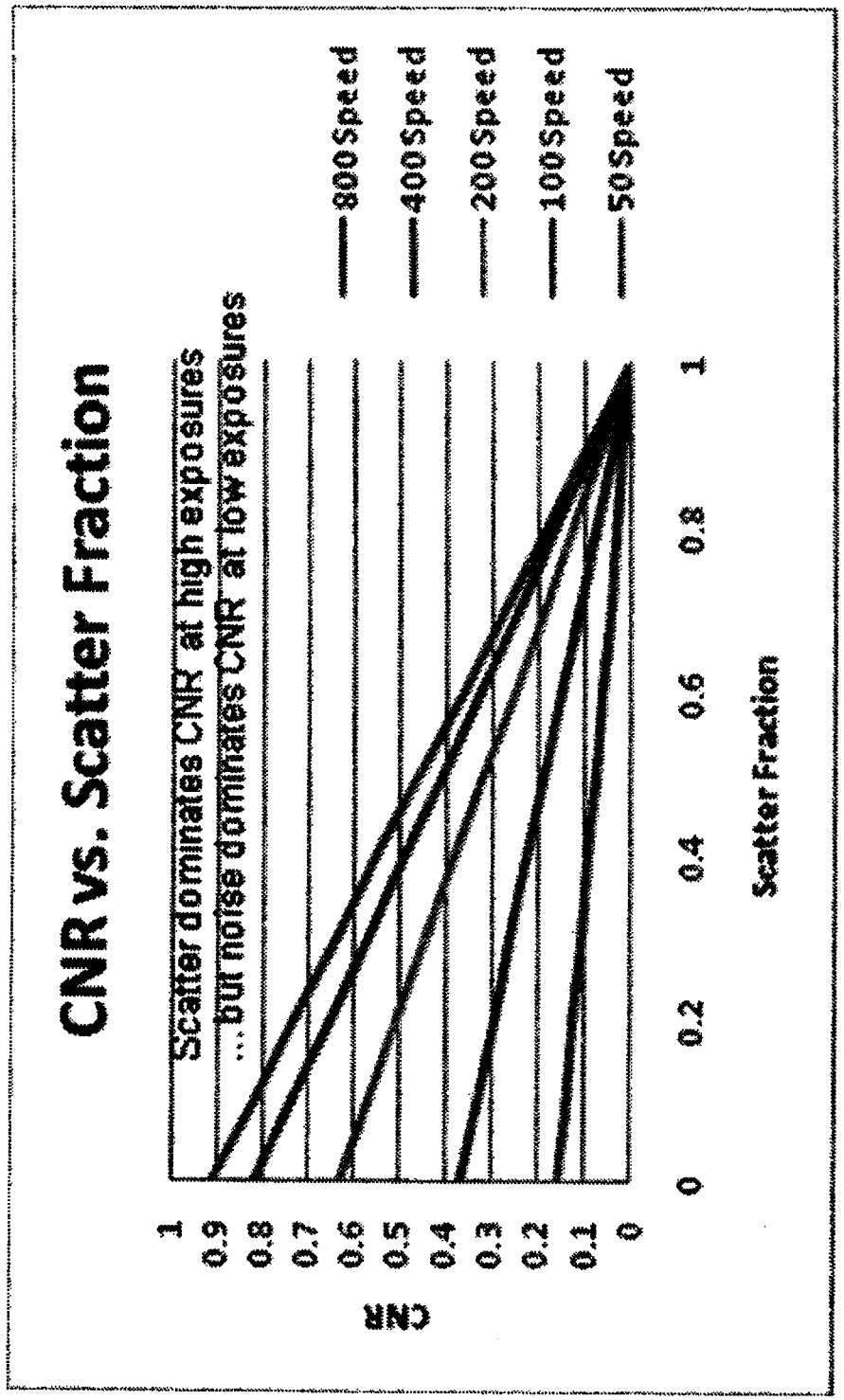
FIG. 5 is a graph that shows how the contrast-to-noise ratio (CNR) relates to scatter.

Contrast is approximately inversely proportional to the percentage of scattered radiation versus total radiation that reaches the imaging receptor and is independent of the exposure level, to the first order. Thus, contrast-to-noise ratio CNR is also approximately inversely proportional to the percentage of scatter, or scatter fraction, as shown in the graph of FIG. 5. As the plots for different film speeds show, scatter is the dominant CNR-related factor at high exposures. Noise is generally more dominant at lower exposures. Scatter fraction relates to patient size or thickness.

Figure 6:
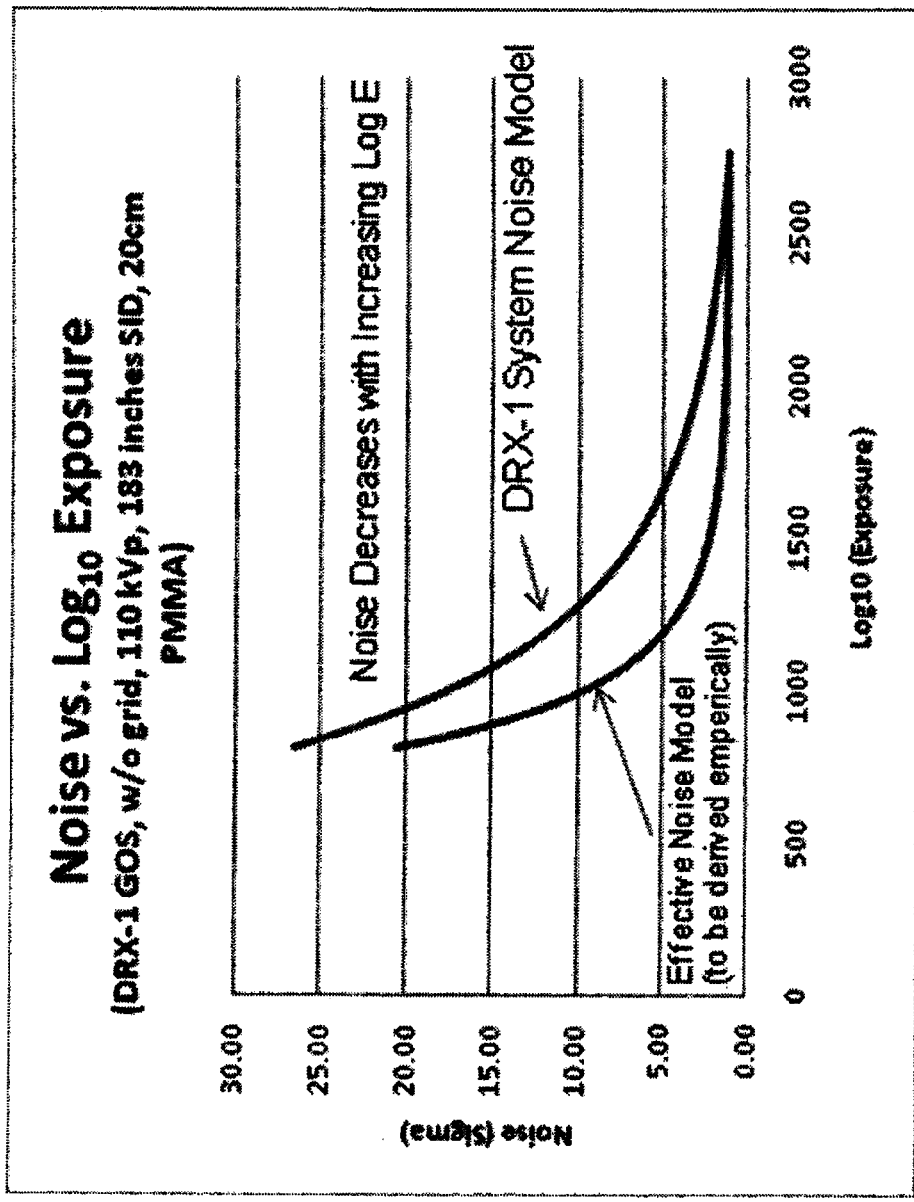
FIG. 6 is a graph that shows noise versus log exposure for typical imaging receivers.
Figure 7:
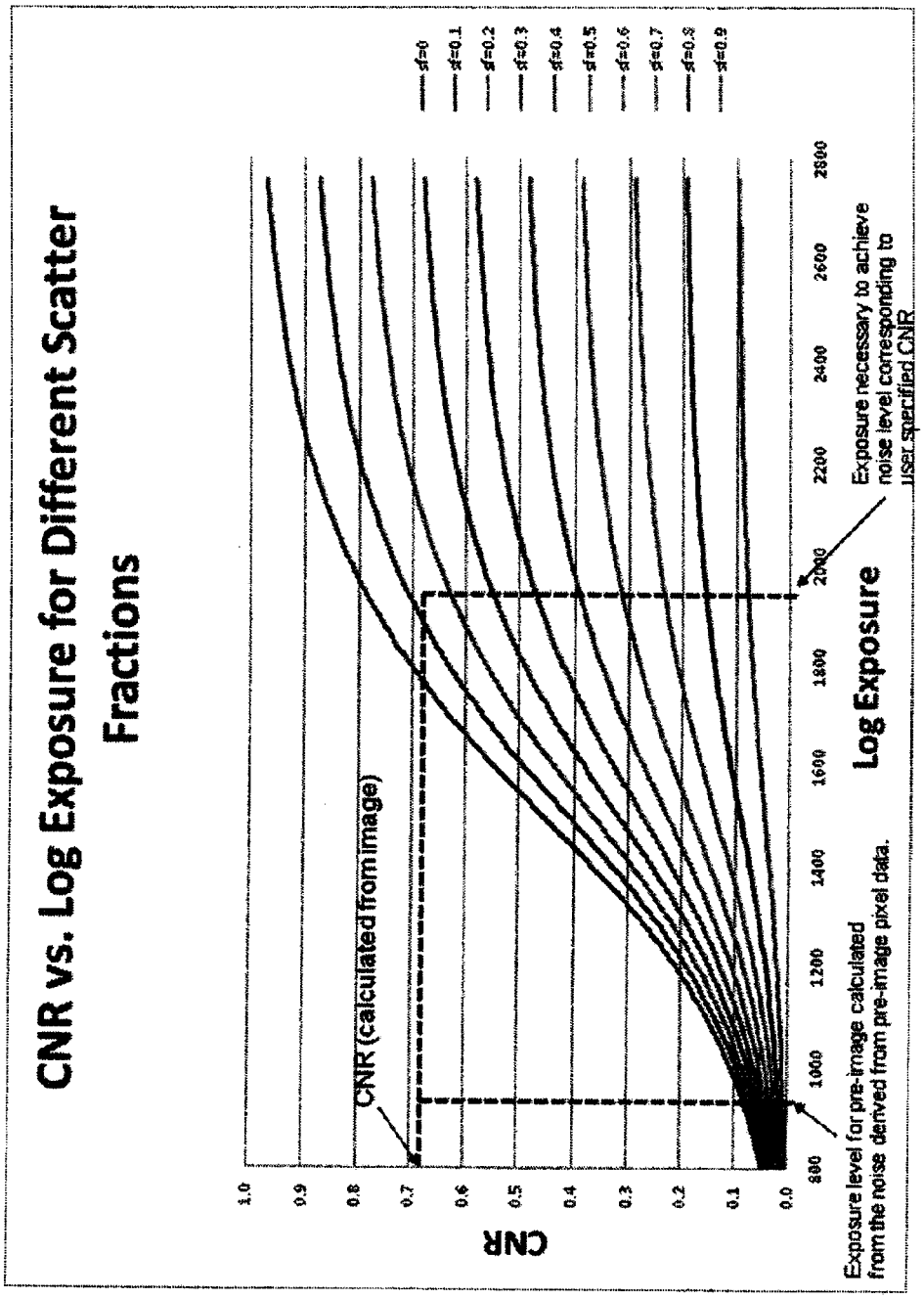
FIG. 7 is a graph that shows how CNR relates to log exposure for different scatter fractions.

As shown in the graph of FIG. 6, noise, as opposed to scatter, decreases with increasing log exposure. Noise decreases rapidly at low exposure levels. At medium to high exposure, noise decrease with log exposure increase is small. These relationships are useful for feedback logic of exemplary embodiments and can be used to help determine whether or not a grid is needed to reduce scatter and to help calculate the necessary exposure for subsequent pulsed exposures. With contrast assumed to be largely independent of noise, and noise related to the exposure level, calculation of contrast in an image from an initial pulsed exposure, and calculation of noise as a function of the exposure level allows calculation of the needed exposure for the next pulse or pulses. Given the signal level needed in the second and subsequent component images for a predetermined CNR, calculation of the needed exposure for those images can be performed. The graph of FIG. 7 shows how the log exposure relates to the CNR and can be computed given a predetermined CNR value. Consistent with an embodiment of the present invention, this relationship is used, in combination with accumulated exposure and image data, to predict the CNR level that can be achieved after a given number of exposures.

For CNR measurement in a chest x-ray, contrast can be calculated as the signal difference between the mediastinal (central chest) region and the clear lung field region, approximately corresponding to an average of the highest signal regions for a band of pixels across the chest radiograph. CNR measurement for other anatomy can be performed in a similar way, with corresponding anatomical structures. Noise can be estimated from a detector model based on the average code value for the same image region. Using the CNR figure of merit as the stopping function therefore provides greater fidelity in driving the system to deliver the optimal diagnostic quality at the lowest possible dose.

However, in practice there may be other figures of merit for image quality that can serve purposes described herein. Other image quality figures of merit include but are not limited to the average code value for a specified region of the image (e.g., as a function for stopping exposure), which could be calculated from a highly under-sampled image, for example, to improve computational speed.

Because exposure control methods of embodiments can be based on an estimate of quality that is derived from actual image data, it is more likely that the captured image will have the requisite quality for diagnostic interpretation. The image quality assessment can be improved over that available using an AEC (e.g., assuming an accurately positioned AEC). The conventional AEC approach merely assures that total exposure to a particular region is at the specified level. Using the CNR figure of merit to assess one or both the contrast and the exposure, the delivered exposure to the patient can have both sufficient contrast and low noise for diagnostic interpretation of the exam, and at a low patient dose.

For exemplary embodiments, a computer program with stored instructions that perform on image data accessed from an electronic memory can be used. As can be appreciated by those skilled in the image processing arts, a computer program implementing embodiments herein (e.g., flowcharts) can be utilized by a suitable, general-purpose computer system, such as a personal computer or workstation. However, many other types of computer systems can be used to execute computer programs implementing embodiments, including networked processors. Computer program for performing embodiments may be stored in a computer readable storage medium. This medium may comprise, for example; magnetic storage media such as a magnetic disk such as a hard drive or removable device or magnetic tape; optical storage media such as an optical disc, optical tape, or machine readable bar code; solid state electronic storage devices such as random access memory (RAM), or read only memory (ROM); or any other physical device or medium employed to store a computer program. Computer program for performing method and/or apparatus embodiments may also be stored on computer readable storage medium that is connected to an image processor by way of the internet or other communication medium. Those skilled in the art will readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, such as database 50 described with reference to FIG. 5A, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Displaying an image requires memory storage. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that computer program products implementing embodiments of this application may make use of various image manipulation algorithms and processes that are well known. It will be further understood that computer program products implementing embodiments of this application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with computer program product implementing embodiments of this application, are not specifically shown or described herein and may be selected from such algorithms, systems, hardware, components and elements known in the art.

According to one aspect of exemplary embodiments, there can be provided a method for obtaining a radiographic image, the method executed at least in part on a computer and comprising: generating a first exposure and acquiring image data from the first exposure as a first component image; generating a second exposure using one or more parameters that are adjusted according to an image quality characteristic of the acquired image data from the first exposure and acquiring image data from the second exposure as a second component image; generating one or more additional exposures and acquiring an additional component image with each additional exposure; and forming a composite image by combining image data content from the first and second component images and the one or more additional component images.

According to one aspect of exemplary embodiments, there can be provided a method for obtaining a radiographic image, the method executed at least in part on a computer and comprising generating a series of pulsed exposures; acquiring image data from each of the pulsed exposures; assessing an image quality characteristic from accumulated image data from the pulsed exposures; and terminating the series of pulsed exposures according to the assessment of the image quality characteristic.

According to one aspect of exemplary embodiments, there can be provided a radiographic imaging apparatus comprising an x-ray source that is energizable to provide a series of exposure pulses, wherein each pulse has a duration within 0.1 seconds; a digital detector that is energizable to provide an image data set corresponding to each exposure pulse; a logic processor that is energizable to acquire each image data set as a component image between exposure pulses, to provide an assessment of image quality from the acquired image data, and to combine the series of component images to form a composite image therefrom; and a display that is in communication with the logic processor and is energizable to display the composite image.

According to one aspect of exemplary embodiments, there can be provided a method for providing operator instructions regarding radiographic image quality, the method executed at least in part on a computer and comprising: generating a pre-image exposure of a patient at a dosage below that required for a diagnostic image; analyzing image data from the pre-image exposure to predict whether or not image contrast from an image at full dosage is within an acceptable range; and prompting the operator to use a grid according to the prediction.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only. The scope of the invention is indicated by the appended claims, and all changes that come within the meaning and range of equivalents thereof are intended to be embraced therein.

What is claimed is:

1. A method for obtaining a radiographic image of a patient's anatomy, the method executed at least in part on a computer and comprising:
   generating a series of N successive exposures [1 . . . N] and acquiring each of N corresponding images as a component image,
   wherein for the third exposure n=3 and for each subsequent exposure n in [1 . . . N], one or more exposure setup parameters is conditioned based on an evaluation of one or more image quality characteristics from at least two previous exposures of the series of N successive exposures [1 ... N].

2. The method of claim 1 wherein the exposure setup parameters are conditioned by adjustment of the one or more exposure setup parameters according to a predictive contrast-to-noise measurement.

3. The method of claim 2 wherein the predictive contrast-to-noise measurement is based on a band of pixels corresponding to the image of a patient's anatomy.

4. The method of claim 2 wherein the adjusted parameters comprise a kVp setting and an mAs setting.

5. The method of claim 1 further comprising:
assessing analyzing image data from a first of the N successive exposures to predict whether image contrast from a composite image is within an acceptable range; and
prompting the operator to use a grid according to the image contrast prediction being outside the acceptable range or combining the series of component images to form the composite image when the image contrast prediction is within the acceptable range.

6. The method of claim 1 further comprising assessing an image quality characteristic from the second exposure or any of the one or more additional exposures and terminating exposure according to the image quality characteristic assessment.

7. The method of claim 1 wherein the image quality characteristic relates to contrast-to-noise ratio.

8. The method of claim 1 wherein the evaluation relates to a contrast-to-noise measurement.

9. The method of claim 1 wherein the one or more exposure setup parameters is conditioned responsive to contrast-to-noise ratio from accumulated image data.

10. A radiographic imaging apparatus comprising:
an x-ray source that is energizable to provide a series of exposure pulses, wherein each pulse has a duration within 0.1 seconds;
a digital detector that is energizable to provide an image data set corresponding to each exposure pulse;
a logic processor that is energizable to acquire each image data set as a component image between exposure pulses, to provide an assessment of image quality from the acquired image data, and to combine the series of component images to form a composite image therefrom; and
a display that is in communication with the logic processor and is energizable to display the composite image.

11. The radiographic imaging apparatus of claim 10 wherein the logic processor further provides a signal indicative of exposure settings for the next exposure pulse.

12. The radiographic imaging apparatus of claim 10 wherein the logic processor further analyzes image data from a first of the series of exposure pulses to predict whether or not image contrast from the composite image is within an acceptable range; and generates an alert to use a grid according to the prediction.

13. The radiographic imaging apparatus of claim 10 wherein the logic processor further assesses an image quality characteristic from the second exposure or subsequent exposure of the series of exposure pulses and terminates the series of exposure pulses and the composite image according to the assessment.

14. The radiographic imaging apparatus of claim 10 wherein the assessment of the image quality characteristic comprises an assessment of contrast-to-noise ratio from accumulated image data.

15. The radiographic imaging apparatus of claim 14 wherein the contrast-to-noise ratio is based on a band of pixels in the acquired image data corresponding to the image of a patient's anatomy.

16. A method for providing operator instructions regarding radiographic image quality at a portable x-ray radiography apparatus, the method executed at least in part on a computer and comprising:
providing a moveable transport frame;
adjustably coupling a first tube head support structure to the moveable transport frame;
generating a pre-image exposure of a patient at a dosage below that required for a diagnostic image;
analyzing image data from the pre-image exposure to predict whether or not image contrast from an image at full dosage is within an acceptable range; and
prompting the operator to use a grid according to the prediction of the image contrast from the image at the full dosage.

17. The method of claim 16 wherein analyzing image data comprises measuring contrast.

18. The radiographic imaging apparatus of claim 10 wherein the logic processor further analyzes image data from at least two image data sets for different component images to provide a signal indicative of exposure settings for subsequent exposure pulse used to acquire an image data set for a subsequent component image, the subsequent exposure pulse being one of the series of exposure pulses.

* * * * *